United States Patent
Haenggi (10) Patent No.: US 9,889,254 B2
(45) Date of Patent: Feb. 13, 2018

(54) DEVICE AND METHOD FOR AUTOMATIC INJECTION AND OCCLUSION DETECTION

(71) Applicant: Roche Diagnostics International AG, Rotkreuz (CH)

(72) Inventor: Roger Haenggi, Lucerne (CH)

(73) Assignee: Roche Diabetes Care, Inc., Indianapolis, IN (US)

( * ) Notice: Subject to any disclaimer, the term of this patent is extended or adjusted under 35 U.S.C. 154(b) by 650 days.

(21) Appl. No.: 14/146,236

(22) Filed: Jan. 2, 2014

(65) Prior Publication Data

US 2014/0121632 A1     May 1, 2014

Related U.S. Application Data

(63) Continuation of application No. PCT/EP2011/061441, filed on Jul. 6, 2011.

(51) Int. Cl.
| | | |
|---|---|---|
| *A61M 5/168* | (2006.01) | |
| *A61M 5/145* | (2006.01) | |
| *A61M 5/50* | (2006.01) | |

(52) U.S. Cl.
CPC ........ *A61M 5/1456* (2013.01); *A61M 5/1452* (2013.01); *A61M 5/14566* (2013.01); *A61M 5/16854* (2013.01); *A61M 5/5086* (2013.01); *A61M 2005/16863* (2013.01); *A61M 2205/332* (2013.01)

(58) Field of Classification Search
CPC .......... A61M 5/16854; A61M 5/16831; A61M 2005/16863; A61M 2205/18; A61M 2205/332

USPC ............................ 604/65–67, 131–155, 505
See application file for complete search history.

(56) References Cited

U.S. PATENT DOCUMENTS

| | | | | | |
|---|---|---|---|---|---|
| 4,657,490 | A | * | 4/1987 | Abbott .............. | A61M 5/14224 417/478 |
| 4,743,228 | A | * | 5/1988 | Butterfield ........ | A61M 5/16859 604/245 |
| 5,074,756 | A | * | 12/1991 | Davis .................... | A61M 5/142 417/45 |
| 5,385,540 | A | * | 1/1995 | Abbott ................ | A61M 1/3664 128/DIG. 3 |
| 5,501,665 | A | * | 3/1996 | Jhuboo ............. | A61M 5/16854 604/65 |
| 5,647,853 | A | * | 7/1997 | Feldmann ......... | A61M 5/16854 604/131 |
| 5,695,473 | A | * | 12/1997 | Olsen ................ | A61M 5/16859 128/DIG. 13 |
| 6,368,314 | B1 | * | 4/2002 | Kipfer ............... | A61M 5/14546 222/309 |

(Continued)

*Primary Examiner* — Gerald Landry, II
(74) *Attorney, Agent, or Firm* — Roche Diabetes Care, Inc.

(57) ABSTRACT

An injection device for injecting automatically a medicament comprises an occlusion detection system with a force measurement unit and two separate occlusion detectors. The occlusion detectors take force measurements at different respective measurement rates and generate occlusion indicating signals based on a set of force measurements taken at the respective measurement rates. The injection device further comprises an alarm generator for generating an occlusion alarm signal in cases where either or both of the occlusion detectors generate an occlusion indicating signal. The two occlusion detectors operating at different measurement rates make it possible to detect occlusions more reliably over a broader range of delivery rates.

18 Claims, 4 Drawing Sheets

(56) References Cited

U.S. PATENT DOCUMENTS

| | | | | |
|---|---|---|---|---|
| 6,423,035 B1* | 7/2002 | Das | A61M 5/1456 | 128/DIG. 1 |
| 6,648,861 B2* | 11/2003 | Platt | A61M 5/16854 | 604/300 |
| 2002/0016569 A1* | 2/2002 | Critchlow | A61M 5/14546 | 604/131 |
| 2003/0205587 A1* | 11/2003 | Tribe | A61M 5/1456 | 222/420 |
| 2004/0133166 A1* | 7/2004 | Moberg | A61M 5/1456 | 604/151 |
| 2005/0096593 A1* | 5/2005 | Pope | A61M 5/1452 | 604/122 |
| 2007/0191770 A1* | 8/2007 | Moberg | A61M 5/14566 | 604/131 |
| 2009/0118667 A1* | 5/2009 | Haueter | A61M 5/14244 | 604/67 |
| 2009/0281497 A1* | 11/2009 | Kamen | A61M 5/1413 | 604/151 |
| 2010/0090843 A1* | 4/2010 | Mandro | A61M 5/1452 | 340/626 |
| 2010/0094222 A1* | 4/2010 | Grant | A61M 5/14244 | 604/151 |
| 2010/0214110 A1* | 8/2010 | Wang | A61M 5/1456 | 340/665 |
| 2010/0245104 A1* | 9/2010 | Oberli | A61M 5/16831 | 340/665 |
| 2012/0078170 A1* | 3/2012 | Smith | A61M 5/14216 | 604/67 |
| 2012/0209197 A1* | 8/2012 | Lanigan | A61M 5/1456 | 604/152 |

\* cited by examiner

DEVICE AND METHOD FOR AUTOMATIC INJECTION AND OCCLUSION DETECTION

CROSS-REFERENCE TO RELATED APPLICATIONS

This application is a continuation of PCT/EP2011/061441, filed Jul. 6, 2011, which is hereby incorporated by reference.

BACKGROUND

The present disclosure generally relates to an injection device for injecting automatically a medicament and a method for detecting an occlusion in the injection device and, in particular, to an automatic injection device and a method for detecting an occlusion in the injection device using a force measurement unit for measuring an injection force.

Generally, it is insulin that is injected into the body of a patient, although other medicaments to be injected over a long period of time can also be injected by the device such as, for example, analgesics, pain killers or cancer drugs.

Automatic injection devices inject a predefined volume of a medicament into the body of a patient at predefined time intervals or delivery rates, respectively, in a continuous or quasi-continuous way. Typically, the delivery rate varies according to an individual schedule such as, for example, according to a pre-programmed circadian profile. Some devices allow the additional injection of larger drug boluses on demand. This volume is withdrawn from a reservoir, generally an exchangeable ampoule, via a pump mechanism and is injected through an injection needle placed in the patient's body. Automatic injection devices may be designed according to the syringe-driver principle. For carrying out an injection, a plunger that is received in a cartridge or ampule is linearly displaced in a controlled way via a typically motor driven pump mechanism with a piston rod that contacts and pushes the piston during operation. If an occlusion is present in such a system, the pressure in the injection system increases, since there is no drop in pressure provided by injections. As a result, a force that is to be applied in the pump mechanism increases over several unsuccessfully performed injections. Thus, a force measurement makes it possible to ascertain whether or not there is an occlusion. If an occlusion occurs, the patient is no longer supplied with a necessary medicament, thus causing potentially severe medical complications. Moreover, since the pump unit operates automatically at predefined time intervals, the pressure in the ampoule and in the feed lines to the patient's body increases, which could cause damage to the injection device. A still greater problem is that, with increasing pressure, the occlusion may eventually break up abruptly and the patient may then receive too large a quantity of the medicament. With a measurement unit that determines an injection force necessary for discharging the medicament, it is possible to ascertain whether an occlusion is present.

For example, such an injection device in which the volume to be injected is discharged by a piston that can be advanced by a spindle driven by an electric motor is known. In order to detect an occlusion during injection, in a first method, a maximum force threshold is predefined and, if it is exceeded, an occlusion alarm is triggered. In a second method, a force increase in a plurality of force values for discharging the injection volume is recorded. If no occlusion is present, then, no increase in force is detectable over a period covering a plurality of injections; only when an occlusion occurs is there an increase over a plurality of measurements. To determine the increase in force, fifteen force values, each determined at identical time intervals, are evaluated.

An automatic injection device with a measurement unit for measuring and storing force values associated with injections of a medicament is also known. An evaluation unit determines an injection occlusion from the measurement values, whereby a switching unit modifies automatically the time interval between individual force measurements depending on evaluation results provided by the evaluation unit. The time interval between the basal releases is maintained constant, e.g. about three minutes, independently of the time intervals for recording the force values. Initially, the force measurements are taken every three minutes in sync with the basal releases and stored over 30 minutes, and only if the evaluation unit determines based on these force measurements a potential occlusion, there is an extension of the time interval for measuring the force values. However, for very low infusion rates, the time interval between the single basal releases has to be increased for typical devices due to a limited injection volume resolution. The time interval between basal releases may, e.g., be extended to 30 minutes for a smallest basal delivery rate of 0.02 IU/h (International Units per hour). Here, the interval between basal releases is longer than the time interval for measuring the force values, resulting in multiple substantially identical measurements between consecutive injections, rather than measurements being in sync with the injections. As a consequence, an occlusion is not detected in this situation.

In addition, some infusion systems provide a check valve or pressure valve between the ampule and the feed line that only opens at a certain opening pressure. After insertion of an ampule into the injection device, the opening pressure has to be built up in the fluidic system by advancing the piston before the feed line can be filled with medicine in a so-called priming phase and injection can start. Once, built up, the fluidic pressure in the ampule is maintained substantially at the opening pressure. Until the opening pressure is built up, the force values, as determined by the measurement unit, continuously increase in a similar way as in case of an occlusion during regular operation. Therefore, such an occlusion detection needs to be deactivated for the time before the actual injections starts.

In some situations, however, an ampule with connected valve and feed line is removed from the device during operation for some time and subsequently re-inserted. When removing the ampule, the opening pressure of the valve, present before, is released. After re-insertion of the ampule, the opening pressure has to be built-up again. Since the device is in a regular operation mode and the occlusion detection is activated, the force increase while building-up the opening pressure may result in a false occlusion alarm.

When inserting an ampule into the device, the ampule is typically fully filled with the plunger in an end position. This, however, is not necessarily the case, for example, if an ampule is filled by a device user only partly, or if readily filled ampules of different filling volumes are commercially available. This is also the case, if an ampule is removed from the device and subsequently re-inserted as described above.

When inserting a new cartridge, a piston rod of the drive mechanism may first be moved forward in a delivery direction, until it contacts the piston of the ampule and building-up the opening pressure of the pressure valve and priming can start. This phase of device operation is referred to as "sniffing phase". During the sniffing phase, the occlusion detection is favorably deactivated. If, however, an ampule is removed during operation and subsequently reinserted, building up the opening pressure and subsequent medicine delivery start immediately without sniffing phase and with the occlusion detection being activated.

Therefore, there is a need to provide an automatically operating injection device and an occlusion detection method which are more flexible and efficient with regards to different basal delivery rates and delivery rate intervals, particularly with regards to low basal delivery rates.

SUMMARY

According to the present disclosure, an injection device and method for injecting automatically a medicament is presented. The injection device can comprise a force measurement unit to measure an injection force; a first occlusion detector to take force measurements at a first measurement rate and to generate a first occlusion indicating signal based on a set of force measurements taken at the first measurement rate; a second occlusion detector to take force measurements at a second measurement rate, lower than the first measurement rate, and to generate a second occlusion indicating signal based on a set of force measurements taken at the second measurement rate; and an alarm generator to generate an occlusion alarm signal in cases where the first occlusion indicating signal is generated by the first occlusion detector or the second occlusion indicating signal is generated by the second occlusion detector.

Accordingly, it is a feature of the embodiments of the present disclosure to provide an automatically operating injection device and an occlusion detection method which are more flexible and efficient with regards to different basal delivery rates and delivery rate intervals, particularly with regards to low basal delivery rates. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

An injection device for injecting automatically a medicament can comprise a force measurement unit to measure an injection force and can further comprise a first occlusion detector to take force measurements at a first measurement rate and to generate a first occlusion indicating signal based on a set of force measurements taken at the first measurement rate; a second occlusion detector to take force measurements at a second measurement rate, lower than the first measurement rate, and to generate a second occlusion indicating signal based on a set of force measurements taken at the second measurement rate; and an alarm generator to generate an occlusion alarm signal in cases where the first occlusion indicating signal is generated by the first occlusion detector and/or (logical "or") the second occlusion indicating signal is generated by the second occlusion detector, i.e. for cases where either one or both of the occlusion detectors indicate a detected occlusion.

Providing the injection device with two occlusion detectors which can operate at different initial measurement rates can have the advantage that occlusions can be detected more reliably over a broader range of delivery rates. Specifically, it can become possible to detect occlusions not only at high delivery rates such as, for example, an injection every three minutes, but also at much lower delivery rates such as, for example, an injection every thirty minutes, depending on how the measurement rates are set.

The injection device can inject the medicament at a variable delivery rate. The first measurement rate can correspond to a defined upper delivery rate limit and the second measurement rate can correspond to a defined lower delivery rate limit lower than the defined upper delivery rate limit.

The first occlusion detector can generate the first occlusion indicating signal based on a set of force measurements taken at the first measurement rate during a first measurement period and the second occlusion detector can generate the second occlusion indicating signal based on a set of force measurements taken at the second measurement rate during a second measurement period longer than the first measurement period.

In one embodiment, the first occlusion detector can generate the first occlusion indicating signal based on a first calculated product of a first vector of weighting factors and the set of force measurements taken at the first measurement rate during the first measurement period and the second occlusion detector can generate the second occlusion indicating signal based on a second calculated product of a second vector of weighting factors and the set of force measurements taken at the second measurement rate during the second measurement period longer than the first measurement period. For example, the first occlusion detector can halve the first measurement rate when the first calculated product is within a first defined threshold range and the second occlusion detector can halve the second measurement rate when the second calculated product is within a second defined threshold range.

In another embodiment, the first occlusion detector can extend the first measurement period by doubling its duration when the first calculated product is within a first defined threshold range and the second occlusion detector can extend the second measurement period by doubling its duration when the second calculated product is within a second defined threshold range. The first occlusion detector can include in the extended first measurement period force measurements taken at the first measurement rate before extending the first measurement period and the second occlusion detector can include in the extended second measurement period force measurements taken at the second measurement rate before extending the second measurement period.

In one embodiment, the first occlusion detector can generate the first occlusion indicating signal when the first calculated product exceeds a first upper threshold value and the second occlusion detector can generate the second occlusion indicating signal when the second calculated product exceeds a second upper threshold value.

In an additional embodiment, the injection device can comprise an occlusion detection system to deduct from the force measurements a force offset value and to detect the occlusions based on the force measurements having the force offset value deducted therefrom.

For detecting an occlusion in an injection device for injecting automatically a medicament, an injection force can be measured; force measurements can be taken at a first measurement rate by a first occlusion detector, and a first occlusion indicating signal can be generated based on a set of force measurements taken at the first measurement rate; force measurements can be taken at a second measurement rate by a second occlusion detector and a second occlusion indicating signal can be generated based on a set of force measurements taken at the second measurement rate; and an occlusion alarm signal can be generated in cases where the first occlusion indicating signal is generated by the first occlusion detector and/or (logical "or") the second occlusion indicating signal is generated by the second occlusion detector.

Figure 1:
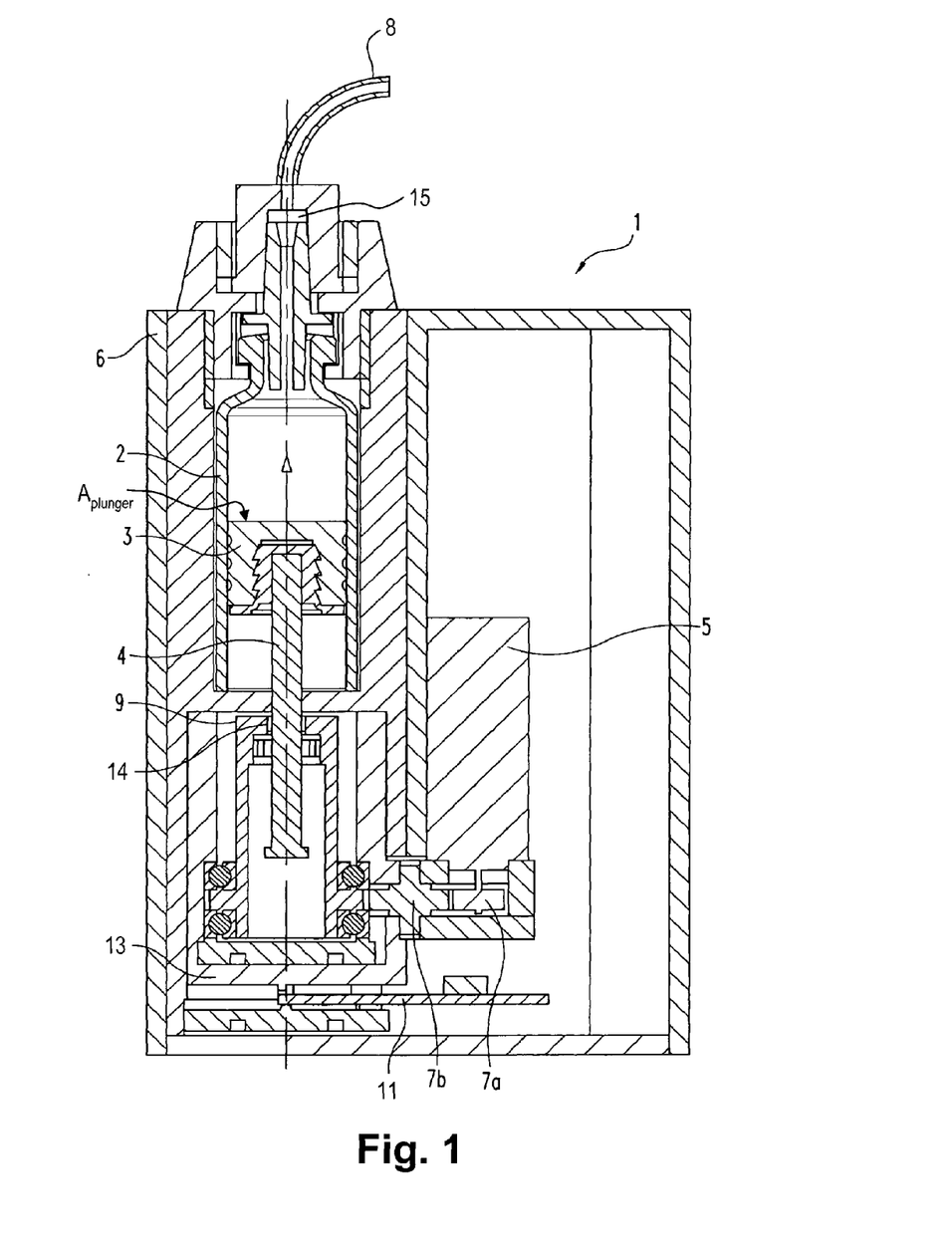
FIG. 1 illustrates a cross section of an injection device for injecting automatically a medicament into a body of a patient according to an embodiment of the present disclosure.
Figure 2:
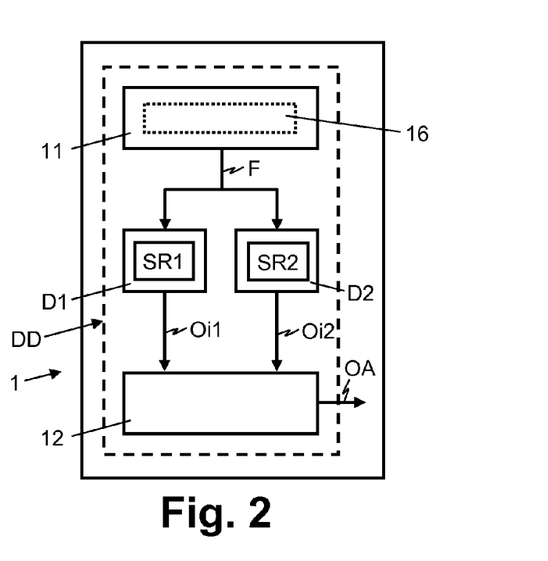
FIG. 2 illustrates a block diagram schematically an automatic injection device with an occlusion detection system having a force measurement unit, two independent occlusion detectors, and an alarm generator according to an embodiment of the present disclosure.

Referring initially to FIGS. 1 and 2, reference numeral 1 can refer to an injection device for injecting automatically a medicament such as, for example, insulin, through a catheter 8 under a patient's skin. FIG. 1 shows an example of the structural configuration of the injection device 1. The injection device 1 can have a pump mechanism accommodated in a housing 6, a reservoir 2 in which the medicament can be stored, and an exchangeable energy supply unit (not shown). The pump unit can have a piston 3 which can lie in the reservoir 2 and which, via a rod-shaped drive member 4, can be driven by an electric motor 5 and toothed wheels 7a and 7b. The electric motor 5 and force transmission elements— toothed wheels 7a and 7b that can act on a sleeve-shaped, further drive member 9 meshing via a thread 14 with the drive member 4—can be arranged on a "free-floating" base 13, which can act on a force sensor 11 operating as force measurement unit for determining, as measurement values or force measurements Fn, the injection force F applied for injection. One skilled in the art can understand that in alternative embodiments different arrangements and implementations of the force sensor or force measurement unit 11, respectively, as well as alternative drive arrangements can be possible. The injection device 1 can further comprise a control unit (not shown) with a controller for the electric motor 5. The control unit can comprise a processor as well as data and program memory.

In one embodiment, the injection device 1 can further comprise a one-way (unidirectional) pressure valve 15, indicated schematically in FIG. 1, arranged at the injection outlet of the injection device 1. The pressure valve 15 can open and let the medicament pass for injection when a defined opening pressure $P_{valve\_opening}$ is reached, such as, for example, $P_{valve\_opening}=0.9$ bar.

As illustrated schematically in FIG. 2, the injection device 1 can comprise an occlusion detection system DD to detect occlusions on the basis of the injection force F measured by the force measurement unit 11. For that purpose, the occlusion detection system DD can comprise several functional modules, including two occlusion detectors D1, D2 to take force measurements by sampling in parallel at different measurement rates SR1, SR2 the injection force F measured by the force measurement unit 11. The measurement rates SR1, SR2 can be sampling rates with different sampling times $$TS1 = \frac{1}{SR1}$$

or $$TS2 = \frac{1}{SR2},$$

respectively.

The occlusion detectors D1, D2 can generate occlusion indicating signals Oi1, Oi2 based on a set of force measurements Fn taken at the respective measurement rates SR1, SR2. The set of force measurements Fn can include a defined equal number N of force measurements F0-F10, e.g. N=11, taken by the occlusion detectors D1, D2 during a measurement period $$TM1 = (N-1) \cdot \frac{1}{SR1}$$

or $$TM2 = (N-1) \cdot \frac{1}{SR2},$$

respectively. For example, the sampling times can be TS1=3 min and TS2=30 min corresponding to measurement periods of TM1=30 min and TM2=300 min, respectively. The sampling times TS1 and TS2 can be set to correspond to the longest and the shortest time interval between consecutive basal releases that may occur for the device. This time interval may, for example, be fixed to about 3 minutes for high delivery rates down to a threshold rate below which the interval can be extended up to a maximum value of about 30 minutes.

With the alarm generator 12, the occlusion detection system DD can comprise a further functional module. The alarm generator 12 can generate an occlusion alarm signal OA, if either or both of the occlusion detectors D1, D2 generate an occlusion indicating signal Oi1, Oi2. Depending on the embodiment, the occlusion alarm signal OA can be used to control, for example, stop, the motor 5, and/or generate a visual and/or audible alarm.

In one embodiment, the occlusion detectors D1, D2 can each be individually activated or deactivated so that the occlusion detection system DD can operate with either one or both of the occlusion detectors D1, D2 in parallel.

Figure 3:
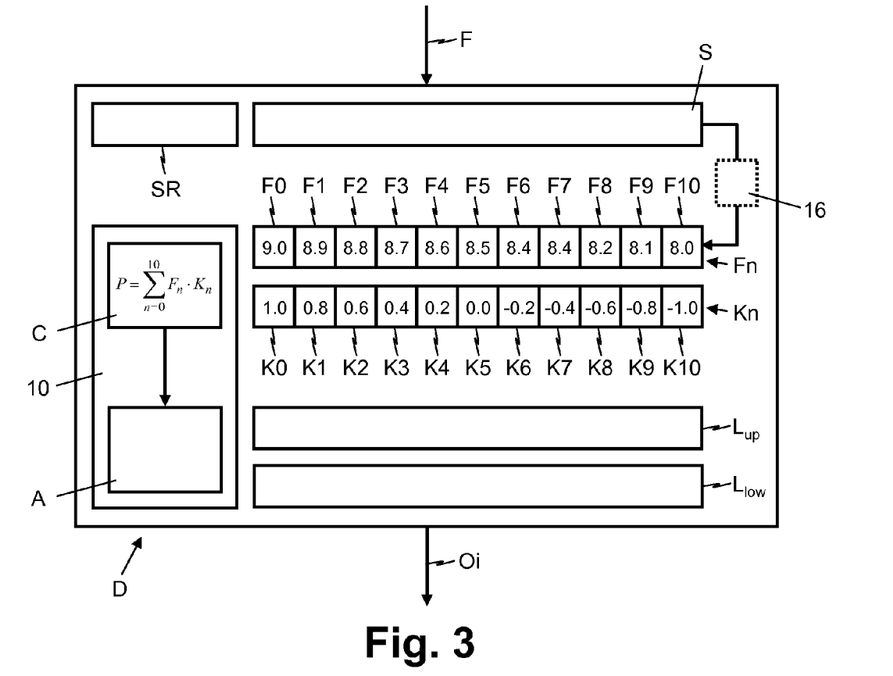
FIG. 3 illustrates a block diagram schematically an occlusion detector for an occlusion detection system of an automatic injection device according to an embodiment of the present disclosure.

In a further embodiment, the occlusion detection system DD can further comprise a force adjustment module 16 to calculate an adjusted force measurement $F_{adjusted}$ by subtracting from the force measurements $F_{measurement}$ in each case a defined force offset value $F_{adjusted}=F_{measurement}-F_{offset}$. As illustrated schematically in FIGS. 2 and 3, the optional adjustment module 16 can be implemented as part of the force measurement unit 11 or the occlusion detectors D1, D2, or as a separate functional module of the occlusion detection system DD arranged between the force measurement unit 11 and one or more occlusion detectors D1, D2. Depending on the embodiment, the force offset value $F_{offset}$ can include a first component $F_{valve\_opening}=P_{valve\_opening} \cdot A_{piston}$ which can depend on the pressure valve 15, specifically the opening pressure $P_{valve\_opening}$ of the pressure valve 15 and the piston area $A_{piston}$ applying the injection force; a second component $F_{piston}$ which can depend on the friction of the piston; a third component $F_{seal}$ which can depend on the friction of a seal arranged in the injection device 1 such as, for example, an X-ring; and/or a fourth component $F_{error}$ representative of an estimated measurement error by the force sensor or force measurement unit 11, respectively, in the force measurement $F_{error}=F_{measurement}-F_{effective}$. For example, considering all four components, the force offset value $F_{offset}$ can be calculated as defined by equation (1):

$$F_{offset}=P_{valve\_opening} \cdot A_{piston}+F_{piston}-F_{seal}-F_{error} \quad (1)$$

Table 1 shows examples of minimum, maximum, and nominal values for the friction force $F_{piston}$ of the piston 3, the friction force associated with the seal $F_{seal}$, the force $F_{valve\_opening}$ for opening the pressure valve 15, and the measurement error $F_{error}$ in the force measurement $F_{measurement}$ whereby all sigma values can be calculated based on the assumption of a CPK-value of 4 (i.e. assuming a symmetrical distribution of +/−4 sigma).

TABLE 1

| Force [N] | Minimum | Maximum | Nominal | Sigma (cpk = 1.33) |
|---|---|---|---|---|
| Friction force of piston $F_{piston}$ | 0.00 | 6.00 | 3.00 | 0.75 |
| Friction force of seal $F_{seal}$ | 0.00 | 3.00 | 1.50 | 0.375 |
| Opening force for pressure valve $F_{valve\_opening}$ | 4.70 | 7.39 | 6.05 | 0.34 |
| Measurement error $F_{error}$ | −1.00 | 1.00 | 0.00 | 0.25 |
| Force offset $F_{offset}$ | 3.80 | 11.30 | 7.55 | 0.94 |

Accordingly, the nominal force offset value to be deducted is about 7.55 N. The standard variation sigma based on CPK-value of 4 can be about 0.94 N for the force offset. In a range for the force offset between about 3.8 N and about 11.3 N, the valve can operate according to specifications.

If subtracting the force offset value $F_{offset}$ from the force measurement $F_{measurement}$ produces a negative result, i.e. if the force offset value $F_{measurement}<F_{offset}$ is greater than force measurement, the force adjustment module 16 can set the adjusted force measurement to zero $F_{adjusted}=0$.

Depending on the embodiment, the occlusion detectors D1, D2, the alarm generator 12, and/or the force adjustment module 16 can be implemented as programmed software modules comprising computer program code for controlling one or more processors (microcontrollers) of the injection device 1, or fully or partly by way of hardware components. It can be pointed out that the force adjustment module 16 can be implemented in an injection device 1 with an occlusion detection system DD comprising and operating with either one or both of the occlusion detectors D1, D2, or with even further occlusion detectors.

In FIG. 3, reference numeral D can refer to an embodiment of the occlusion detectors D1, D2. As illustrated in FIG. 3, embodiment D of the occlusion detectors D1, D2 can comprise several functional modules including a sampling module S and a control module 10 with a computing module C and an analyzing module A. The embodiment D of the occlusion detectors D1, D2 can further comprise a memory unit SR for storing the current measurement (sampling) rate SR1, SR2, an array of memory units F0-F10 for storing the set of force measurements Fn taken by the sampling module S at the current measurement rates SR1, SR2, an array of memory units K0-K10 for storing a set of weighting factors Kn, and memory units for storing values of an upper limit $L_{up}$ and a lower limit $L_{low}$.

The computing module C can calculate from the set of force measurements Fn and the vector of weighting factors Kn the scalar or dot product $$P = \sum_{n=0}^{10} F_n \cdot K_n.$$

The analyzing module A can compare the calculated scalar or dot product P to the current values of the upper limit $L_{up}$ and the lower limit $L_{low}$ and can generate an occlusion indicating signal Oi, Oi1, Oi2 depending on the result of that comparison, as will be described below.

Depending on the embodiment, the sampling module S and/or the control module 10 with the computing module C and analyzing module A can be implemented as programmed software modules comprising computer program code for controlling one or more processors (microcontrollers) of the injection device 1, or fully or partly by way of hardware components.

Figure 4:
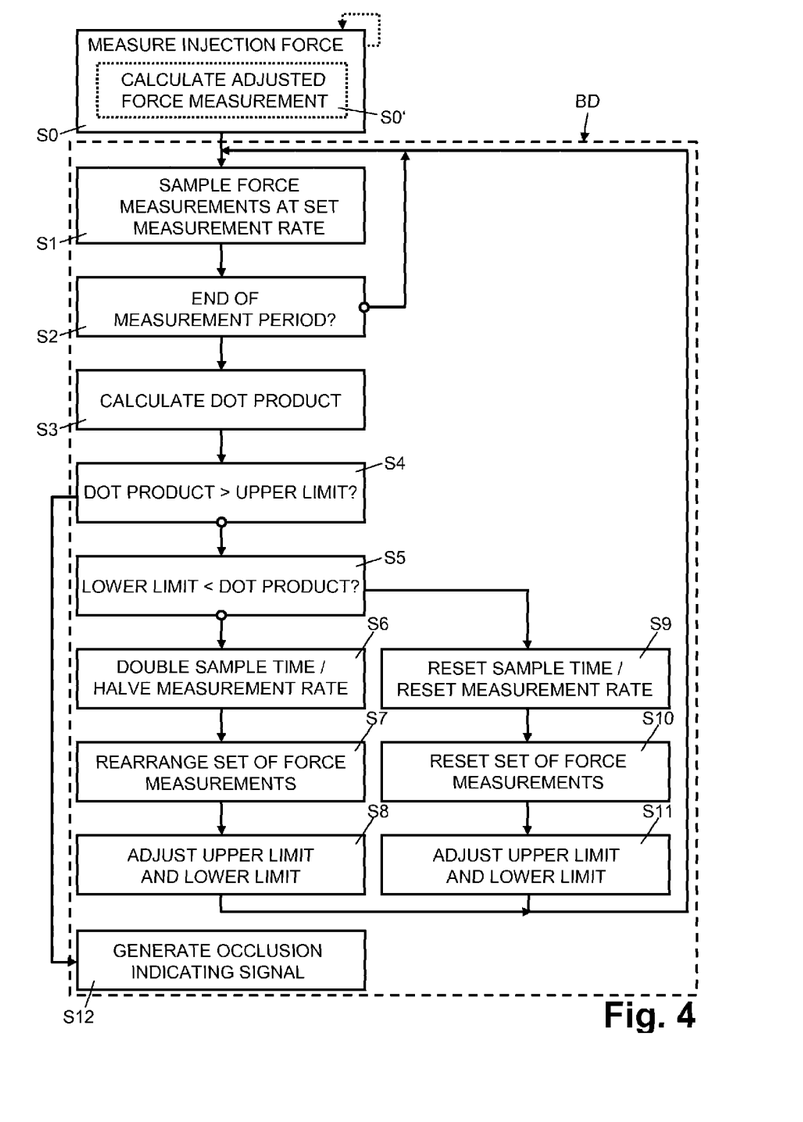
FIG. 4 illustrates a flow diagram for detecting an occlusion in an automatic injection device according to an embodiment of the present disclosure.

In the following paragraphs, described with reference to FIG. 4 are possible sequences of steps performed by the occlusion detection system DD or its functional modules, respectively, for detecting an occlusion in the injection device 1.

In step S0, the injection force F can be measured continuously or periodically by the force sensor 11 operating as force measurement unit. Optionally, for example, if the injection device 1 is provided with a pressure valve 15 at its outlet, in step S0', the force measurement $F_{measurement}$ can be adjusted by the adjustment module 16 calculating an adjusted force measurement $F_{adjusted}=F_{measurement}-F_{offset}$, as described above.

In one embodiment, in addition or as an alternative to compensating for the opening pressure $P_{valve\_opening}$ of the valve 15 by subtracting a respective force offset from the force measurement $F_{measurement}$ operation of the occlusion detection system DD or the occlusion detectors D1, D2, respectively, can be delayed by a defined time delay $T_{delay}$ after the priming phase. The time delay $T_{delay}$ can be implemented by the control module 10 based on a set delay parameter Delay and can ensure that there can be no incorrect alarms after the sniffing phase, if there is no priming phase. The delay parameter Delay can be expressed in [IU]; this can mean that the occlusion detection system DD or the occlusion detectors D1, D2, respectively, cannot be active after the sniffing phase as long as the amount of IUs, indicated by the delay parameter Delay, has not been administered. The control module 10 can determine the time delay $T_{delay}$ based on the set basal rate BasalRate, defined in [UI/h] and the delay parameter Delay using equation (2), where $T_{StartBasal}$ can be set to zero:

$$T_{delay} = \frac{\text{Delay} \cdot 3600}{\text{BasalRate}} + T_{StartBasal} \quad (2)$$

In block BD, steps S1-S12 can be performed for detecting occlusions in the injection device 1.

In step S1, at the set current measurement rate SR1, SR2, the occlusion detector D1, D2 can take a force measurement Fn from the force measurement unit 11. The force measurements Fn can be taken in sync with the injection of the medicament such as, for example, at a defined duration of time, for example, one second, before an injection. In other words, the injection force F can be sampled in sync with the injection of the medicament. In correspondence with its time or position n in the measurement period TM1, TM2 the force measurement Fn can be stored in the memory units F0-F10. For example, in the embodiment D shown in FIG. 3, the first or oldest force measurement of the current measurement period TM1, TM2 can be stored in memory unit F10 ("8.0"), whereas the last or newest force measurement of the current measurement period TM1, TM2 can be stored in memory unit F0 ("9.0").

In step S2, the control module 10 can check whether the end of the current measurement period TM1, TM2 has been reached, i.e. whether the set of force measurements Fn for the current measurement period TM1, TM2 is complete and can hold the defined number of force measurements, e.g. n=11, taken during the current measurement period TM1, TM2 at the current measurement rate SR1, SR2. If the current measurement period TM1, TM2 has not ended, processing can continue in step S1 by taking the next force measurement Fn. Otherwise, if the current measurement period TM1, TM2 has ended, processing can continue in step S3.

In step S3, the computing module C can calculate from the current set of force measurements Fn and the vector of weighting factors Kn the scalar or dot product $$P = \sum_{n=0}^{10} F_n \cdot K_n.$$

Depending on the embodiment, an identical or different set of weighting factors Kn can be used for the detectors D1, D2.

In step S4, the analyzing module A can check whether the value of the calculated dot product P is greater than the upper limit $P > L_{up}$. If the dot product P is greater than the upper limit $P > L_{up}$, processing can continue in step S12 with generating an occlusion indicating signal Oi. Otherwise, if the dot product P is not greater than the upper limit $P \leq L_{up}$, processing can continue in step S5.

In step S5, the analyzing module A can check whether the value of the calculated dot product P is lower than the lower limit $P < L_{low}$. If the dot product P is lower than the lower limit $P < L_{low}$, processing can continue in step S9; otherwise, if the dot product P is not lower than the lower limit, i.e. the dot product is within the range of the upper and lower limits $L_{low} \leq P \leq L_{up}$, processing can continue in step S6.

In step S6, the control module 10 can increase the measurement period TM1, TM2 for the respective occlusion detector D1, D2 that had a dot product within the value range of upper and lower limits $L_{low} \leq P \leq L_{up}$. Specifically, the respective measurement period TM1, TM2 and sample time TS1, TS2 can be doubled and the corresponding measurement rate SR1, SR2 can be halved accordingly. Respective modes "Mode1", "Mode2", "Mode4", "Mode8", and "Mode16" indicate how many times the respective measurement period TM1, TM2 or sample time TS1, TS2 have been multiplied, for example, "Mode 1" can indicate that the current measurement period TM1, TM2 or sample time TS1, TS2 can correspond to the initial measurement period TM1, TM2 or sample time TS1, TS2, respectively; whereas "Mode 8" can indicate that the current measurement period TM1, TM2 or sample time TS1, TS2 can correspond to an eight-fold of the initial measurement period TM1, TM2 or sample time TS1, TS2, respectively.

In step S7, the control module 10 can rearrange the set of force measurements stored in the memory units F0-F10 in accordance with the extended measurement period TM1, TM2 and corresponding measurement rate SR1, SR2. Specifically, kept can be those force measurements F0, F2, F4, F6, F8, F10 which were stored for the measurement period TM1, TM2 before the extension, but were taken in sync with the new measurement rate; while deleted can be those force measurements F9, F7, F5, F3, F1 which were not taken in sync with the new measurement rate. Table 2, illustrates how the set of force measurements can be rearranged through this adjustment process by showing contents of the memory units F0-F10 for before and after the adjustment or rearrangement process, in the transition from "Mode 1" to "Mode 2", whereby those values that are kept can be indicated in bold.

TABLE 2

| Before (Mode 1) | |
|---|---|
| F10 | 8.0 |
| F9 | 8.1 |
| F8 | 8.2 |
| F7 | 8.4 |
| F6 | 8.4 |
| F5 | 8.5 |
| F4 | 8.6 |
| F3 | 8.7 |
| F2 | 8.8 |
| F1 | 8.9 |
| F0 | 9.0 |
| After (Mode 2) | |
| F10 | 8.0 |
| F9 | 8.2 |
| F8 | 8.4 |
| F7 | 8.6 |
| F6 | 8.8 |
| F5 | 9.0 |
| F4 | 0.0 |
| F3 | 0.0 |
| F2 | 0.0 |
| F1 | 0.0 |
| F0 | 0.0 |

As is illustrated in Table 2, the contents of F10, i.e. the oldest and first force measurement in the set, can remain the same, whereas due to the slower measurement rate the contents of F8, F6, F4, F2 and F0 can become the contents of F9, F8, F7, F6 or F5, respectively.

Likewise, Table 3 illustrates the adjustment and rearrangement of the set of force measurements stored in the memory units F0-F10 when the initial measurement period TM1, TM2 ("Mode 1") is doubled ("Mode 2"), quadrupled ("Mode 4") and octuplicated ("Mode 8") in length, respectively.

TABLE 3

| Initial measurement period (Mode 1) | | Doubled measurement period (Mode 2) | | Quadrupled measurement period (Mode 4) | | Octuplicated measurement period (Mode 8) | |
|---|---|---|---|---|---|---|---|
| F10 | 8.0 | F10 | 8.0 | F10 | 8.0 | F10 | 8.0 |
| F9 | 8.1 | F9 | 8.2 | F9 | 8.4 | F9 | 0.0 |
| F8 | 8.2 | F8 | 8.4 | F8 | 8.8 | F8 | 0.0 |
| F7 | 8.4 | F7 | 8.6 | F7 | 0.0 | F7 | 0.0 |
| F6 | 8.4 | F6 | 8.8 | F6 | 0.0 | F6 | 0.0 |
| F5 | 8.5 | F5 | 9.0 | F5 | 0.0 | F5 | 0.0 |
| F4 | 8.6 | F4 | 0.0 | F4 | 0.0 | F4 | 0.0 |
| F3 | 8.7 | F3 | 0.0 | F3 | 0.0 | F3 | 0.0 |
| F2 | 8.8 | F2 | 0.0 | F2 | 0.0 | F2 | 0.0 |
| F1 | 8.9 | F1 | 0.0 | F1 | 0.0 | F1 | 0.0 |
| F0 | 9.0 | F0 | 0.0 | F0 | 0.0 | F0 | 0.0 |

In step S8, the control module 10 can adjust the values of upper limit $L_{up}$ and the lower limit $L_{low}$ that can be applicable to the current length of the measurement period TM1, TM2. Subsequently, processing can continue in step S1 by sampling the injection force F at the new sample time TS1, TS2 or sampling rate SR1, SR2, respectively. Table 4 shows examples of defined values for the upper limit $L_{up}$ and the lower limit $L_w$ as well as the corresponding sample times TS1, TS2 for the measurement periods TM1, TM2 according to Modes 1, 2, 4, 8 and 16, respectively.

TABLE 4

| | Measurement mode | | | | |
|---|---|---|---|---|---|
| | 1 | 2 | 4 | 8 | 16 |
| upper limit $L_{up}$ | 8.03 | 7.7 | 7.04 | 5.75 | 4.4 |
| lower limit $L_{low}$ | 0.275 | 0.55 | 1.1 | 2.2 | 4.4 |
| Sample time TS1, TS2 | 3/30 | 6/60 | 12/120 | 24/240 | 48/480 |
| Measurement period TM1, TM2 | 30/300 | 60/600 | 120/1200 | 240/2400 | 480/4800 |

In step S9, the control module 10 can reset the measurement period TM1, TM2 for the respective occlusion detector D1, D2 that had a dot product below the lower limit $L_{low}$. Specifically, the respective measurement period TM1, TM2 and sample time TS1, TS2, and accordingly the corresponding measurement rate SR1, SR2, can be reset to their initial values of "Mode 1".

In step S10, the control module 10 can reset the set of force measurements Fn stored in the memory units F0-F10 to zero.

In step S11, the control module 10 can reset the values of upper limit $L_{up}$ and the lower limit $L_{10}$ to their initial values of "Mode 1". Subsequently, processing can continue in step S1 by sampling the injection force F at the reset sample time TS1, TS2 or sampling rate SR1, SR2, respectively.

In step S12, the control module 10 can generate an occlusion indicating signal Oi, Oi1, Oi2 for the respective occlusion detector D1, D2 that had a dot product above the upper limit $L_{up}$.

Responsive to an occlusion indicating signal Oi, Oi1, Oi2 from either or both of the occlusion detectors D1, D2, the alarm generator 12 can generate an occlusion alarm signal OA.

Figure 5:
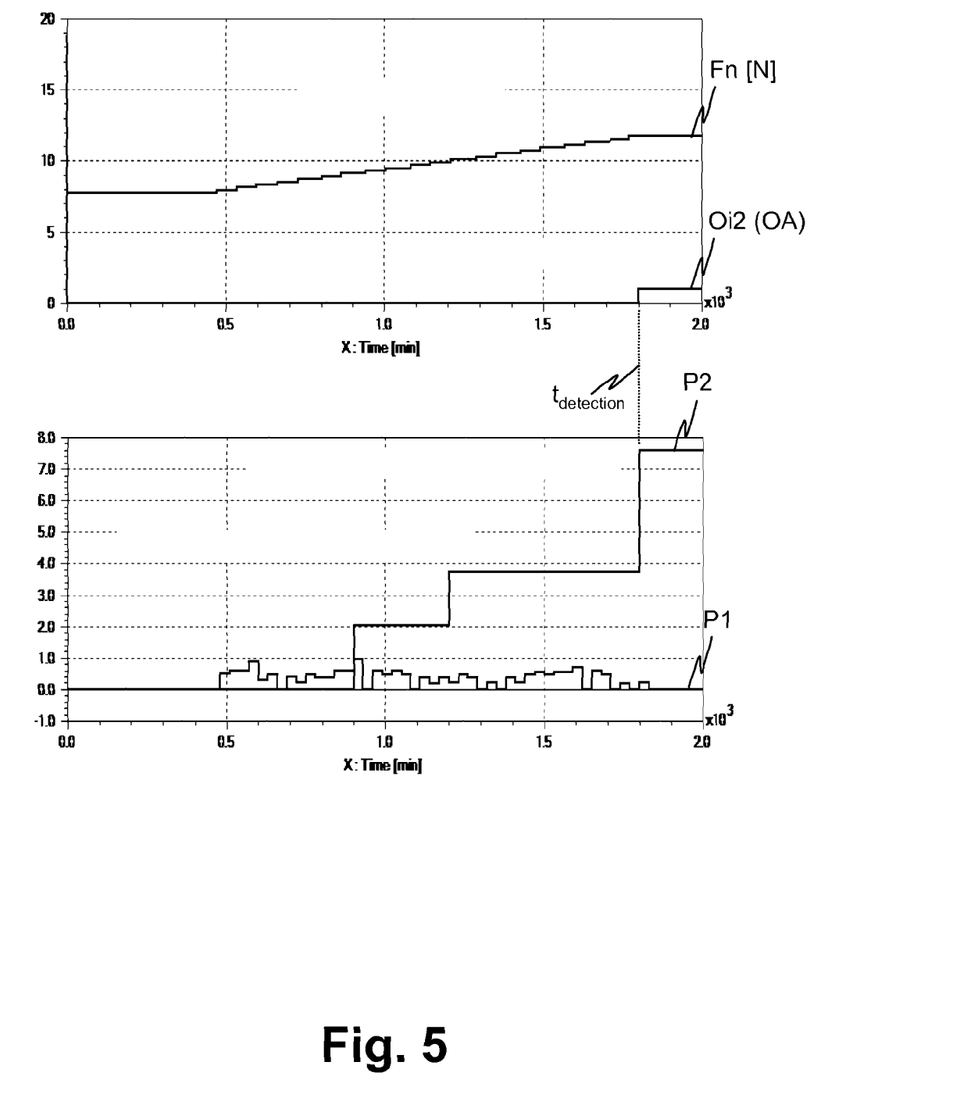
FIG. 5 illustrates graphs of an example of occlusion detection including the temporal course of force measurements and different dot products generated by occlusion detectors from force measurements taken at different measurement rates according to an embodiment of the present disclosure.

FIG. 5 shows an example of occlusion detection by the occlusion detection system DD for a basal delivery rate of about 0.02 [IU/h], a basal delivery interval of about 2 [h], a priming volume of about 0 [IU], and a delay parameter of about 0.5 [IU]. The occlusion detector D1 can be set to a take force measurements Fn at a measurement rate SR1 corresponding to a sampling time TS1 of about 3 minutes. The occlusion detector D2 can be set to a take force measurements Fn at a measurement rate SR2 corresponding to a sampling time TS2 of about 30 minutes.

Specifically, FIG. 5 illustrates in the top graph the temporal course of the force measurements $F_n$ in [N] (depending on the embodiment adjusted or not adjusted by the force offset) after a time delay. The top graph can further show the occlusion indicating signal Oi2 generated by the occlusion detector D2. In the bottom graph, FIG. 5 illustrates the dot product P1 generated by the occlusion detector D1 operating at the sampling time TS1 of about 3 minutes and the dot product P2 generated by the occlusion detector D2 operating at the sampling time TS2 of about 30 minutes. As can be seen in FIG. 5, the occlusion detector D1 operating at the sampling time TS1 of about 3 minutes can always stay in the 30 minute evaluation period and can, therefore, not detect an occlusion. However, in the present example, the occlusion detector D2 operating at the sampling time TS2 of about 30 minutes can detect an occlusion and, thus, can generate a corresponding occlusion indicating signal Oi2 at the detection time $t_{detection}$ for which the alarm generator 12 can be generate a corresponding occlusion alarm signal OA. For a high delivery rate, in contrast, an occlusion can be detected by occlusion detector D1, but not by occlusion detector D2. The arrangement of more than one occlusion detector can allow the detection of occlusions over a large range of basal delivery rates. In addition to the occlusion detectors as described herein, a further occlusion detector with a fixed force threshold value may be present as fallback for situations where the somewhat more sophisticated occlusion detectors fail to correctly detect the presence of an occlusion due to a data artefact or the like.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

It should be noted that, the occlusion detectors D1, D2 can each be associated with an array of eleven array elements for measuring, recording, and processing a set of eleven force measurements Fn over a measurement period TM1, TM2 including ten times the sample time TS1, TS2; however, one skilled in the art can understand that the occlusion detectors D1, D2 and the array can alternatively be configured for different numbers of force measurements Fn and measurement periods TM1, TM2, such as, for example, an array with nine or seventeen elements for recording and processing a corresponding number of force measurements Fn over a measurement period TM1, TM2 including eight or sixteen times the respective sample time TS1, TS2 Likewise, in the described examples, the initial sampling times TS1, TS2 can be set to correspond to the defined lower delivery rate limit (minimum delivery rate) and the defined upper delivery rate limit (maximum delivery rate) of three and thirty minutes, respectively, but one skilled in the art can understand that different values for the initial sampling times TS1, TS2 or corresponding minimum and maximum delivery rates can be possible. Moreover, the computer program code can be associated with specific functional modules and the sequence of the steps can be presented in a specific order, one skilled in the art can understand, however, that the computer program code may be structured differently and that the order of at least some of the steps could be altered, without deviating from the scope of the invention. Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. An injection device for injecting automatically a medicament, the injection device comprising:
    a force measurement unit to measure an injection force;
    a first occlusion detector to take force measurements at a first measurement rate and to generate a first occlusion indicating signal based on a set of force measurements taken at the first measurement rate;
    a second occlusion detector to take force measurements at a second measurement rate, lower than the first measurement rate, and to generate a second occlusion indicating signal based on a set of force measurements taken at the second measurement rate; and
    an alarm generator to generate an occlusion alarm signal in cases where the first occlusion indicating signal is generated by the first occlusion detector or the second occlusion indicating signal is generated by the second occlusion detector.

2. The injection device according to claim 1, wherein the injection device injects the medicament at a variable delivery rate where the first measurement rate corresponds to a defined upper delivery rate limit and the second measurement rate corresponds to a defined lower delivery rate limit which is lower than the defined upper delivery rate limit.

3. The injection device according to claim 1, wherein the first occlusion detector generates the first occlusion indicating signal based on a set of force measurements taken at the first measurement rate during a first measurement period and the second occlusion detector generates the second occlusion indicating signal based on a set of force measurements taken at the second measurement rate during a second measurement period longer than the first measurement period.

4. The injection device according to claim 3, wherein the first occlusion detector generates the first occlusion indicating signal based on a first calculated product of a first vector of weighting factors and the set of force measurements taken at the first measurement rate during a first measurement period and the second occlusion detector generates the second occlusion indicating signal based on a second calculated product of a second vector of weighting factors and the set of force measurements taken at the second measurement rate during a second measurement period longer than the first measurement period.

5. The injection device according to claim 4, wherein the first occlusion detector halves the first measurement rate when the first calculated product is within a first defined threshold range and the second occlusion detector halves the second measurement rate when the second calculated product is within a second defined threshold range.

6. The injection device according to claim 4, wherein the first occlusion detector extends the first measurement period by doubling its duration when the first calculated product is within a first defined threshold range and the second occlusion detector extends the second measurement period by doubling its duration when the second calculated product is within a second defined threshold range.

7. The injection device according to claim 6, wherein the first occlusion detector includes in the extended first measurement period force measurements taken at the first measurement rate before extending the first measurement period and the second occlusion detector includes in the extended second measurement period force measurements taken at the second measurement rate before extending the second measurement period.

8. The injection device according to claim 4, wherein the first occlusion detector generates the first occlusion indicating signal when the first calculated product exceeds a first upper threshold value and the second occlusion detector generates the second occlusion indicating signal when the second calculated product exceeds a second upper threshold value.

9. The injection device according to claim 1, further comprising:
    an occlusion detection system to deduct from the force measurements a force offset value and to detect the occlusions based on the force measurements having the force offset value deducted therefrom.

10. A method of detecting an occlusion in an injection device for injecting automatically a medicament, the method comprising:
    measuring an injection force;
    taking force measurements at a first measurement rate by a first occlusion detector and generating a first occlusion indicating signal based on a set of force measurements taken at the first measurement rate;
    taking force measurements at a second measurement rate, lower than the first measurement rate, by a second occlusion detector and generating a second occlusion indicating signal based on a set of force measurements taken at the second measurement rate; and
    generating an occlusion alarm signal when where the first occlusion indicating signal is generated by the first occlusion detector or the second occlusion indicating signal is generated by the second occlusion detector.

11. The method according to claim 10, wherein the medicament is injected at a variable delivery rate, the first measurement rate corresponds to a defined upper delivery rate limit and the second measurement rate corresponds to a defined lower delivery rate limit which is lower than the defined upper delivery rate limit.

12. The method according to claim 10, wherein the first occlusion indicating signal is generated by the first occlusion detector based on a set of force measurements taken at the first measurement rate during a first measurement period and the second occlusion indicating signal is generated by the second occlusion detector based on a set of force measurements taken at the second measurement rate during a second measurement period longer than the first measurement period.

13. The method according to claim 12, wherein the first occlusion indicating signal is generated by the first occlusion detector based on a first calculated product of a first vector of weighting factors and the set of force measurements taken at the first measurement rate during a first measurement period and the second occlusion indicating signal is generated by the second occlusion detector based on a second calculated product of a second vector of weighting factors and the set of force measurements taken at the second measurement rate during a second measurement period longer than the first measurement period.

14. The method according to claim 13, wherein the first measurement rate is halved by the first occlusion detector when the first calculated product is within a first defined threshold range and the second measurement rate is halved by the second occlusion detector when the second calculated product is within a second defined threshold range.

15. The method according to claim 13, wherein the first measurement period is extended by the first occlusion detector doubling its duration when the first calculated product is within a first defined threshold range and the second measurement period is extended by the second occlusion detector doubling its duration when the second calculated product is within a second defined threshold range.

16. The method according to claim 15, wherein in the extended first measurement period included by the first occlusion detector are force measurements taken at the first measurement rate before extending the first measurement period and in the extended second measurement period included by the second occlusion detector are force measurements taken at the second measurement rate before extending the second measurement period.

17. The method according to claim 14, wherein the first occlusion indicating signal is generated by the first occlusion detector when the first calculated product exceeds a first upper threshold value and the second occlusion indicating signal is generated by the second occlusion detector when the second calculated product exceeds a second upper threshold value.

18. The method according to claim 10, further comprising: deducting a force offset value from the force measurements and detecting the occlusions based on the force measurements having the force offset value deducted therefrom.

* * * * *